United States Patent [19]

Fabinski et al.

[11] 4,288,693

[45] Sep. 8, 1981

[54] NONDISPERSIVE INFRARED GAS ANALYZER

[75] Inventors: Walter Fabinski, Kriftel; Udo Deptolla, Ober Olm, both of Fed. Rep. of Germany

[73] Assignee: Hartmann & Braun Aktiengesellschaft, Frankfurt am Main, Fed. Rep. of Germany

[21] Appl. No.: 46,549

[22] Filed: Jun. 7, 1979

[30] Foreign Application Priority Data

Jun. 22, 1978 [DE] Fed. Rep. of Germany ....... 2827345
Mar. 12, 1979 [DE] Fed. Rep. of Germany ....... 2909688

[51] Int. Cl.³ .................... G01J 1/00; G01N 21/25
[52] U.S. Cl. ................................. 250/345; 356/414
[58] Field of Search ............... 250/343, 344, 345, 373; 356/414

[56] References Cited

U.S. PATENT DOCUMENTS

| | | | |
|---|---|---|---|
| 2,761,067 | 8/1956 | Troy | 250/432 |
| 3,103,586 | 9/1963 | Ovrebo et al. | 250/345 |
| 3,916,195 | 10/1975 | Burch et al. | 250/345 |
| 4,157,470 | 6/1979 | Kotaka et al. | 250/345 |

FOREIGN PATENT DOCUMENTS

2552165 5/1977 Fed. Rep. of Germany.

Primary Examiner—Alfred E. Smith
Assistant Examiner—Carolyn E. Fields
Attorney, Agent, or Firm—Smyth, Pavitt, Siegemund & Martella

[57] ABSTRACT

The cross sensitivity of a two-beam infrared gas analyzer is eliminated by using two differently long cells for the measuring gas in the two beam paths and by using an interference filter at least in the beam path containing the longer cell; the filter, however, does not filter the entire beam in that path.

6 Claims, 2 Drawing Figures

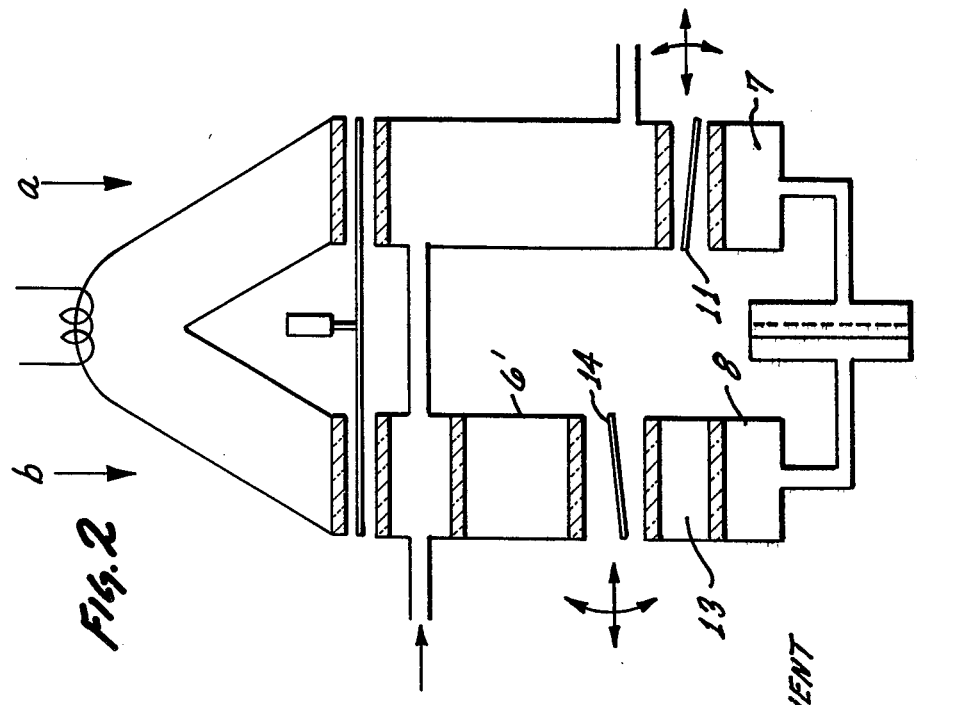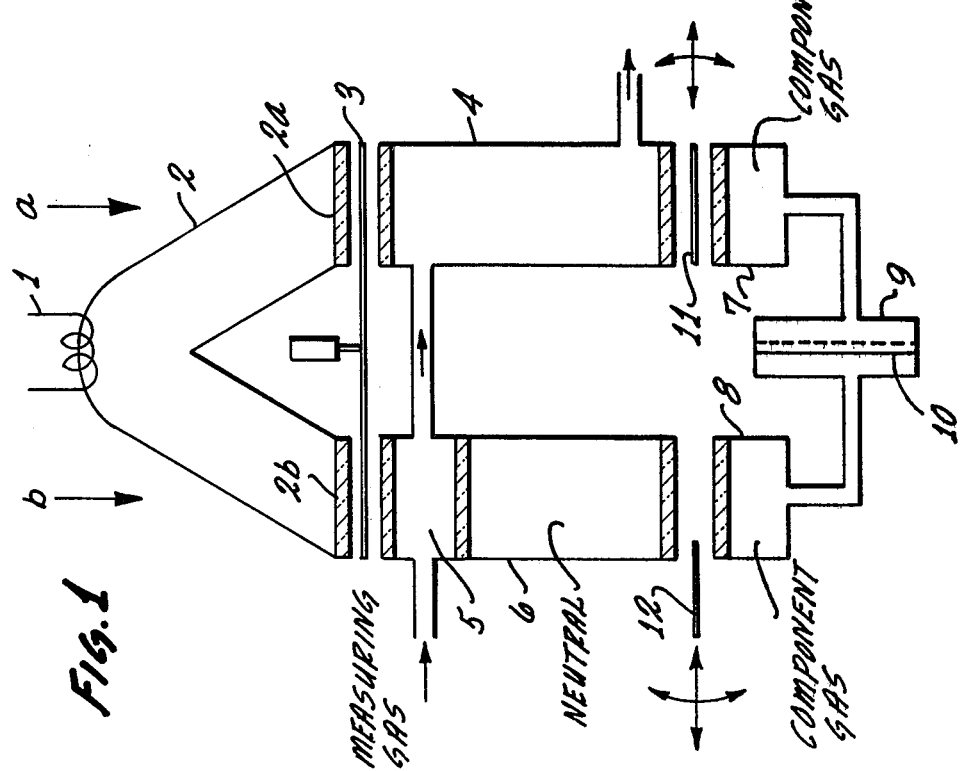

NONDISPERSIVE INFRARED GAS ANALYZER

BACKGROUND OF THE INVENTION

The present invention relates to a nondispersive infrared gas analyzer.

Gas analyzers of the type to which the invention pertains use the following principle. A test or sample beam of radiation traverses the substance (measuring gas) to be analyzed, wherein a portion of that radiation is frequency selectively absorbed. The, thus, attenuated radiation is passed on to a receiving cell which, likewise, absorbs radiation at the same frequency as the particular substance to be detected, but the cell content should not have any common absorption band with the other components in the substance to be analyzed. In practice, one uses in the receiver cell a specific quantity of the substance to be detected. Upon absorbing radiation, the receiving cell will undergo a change in temperature, pressure, or volume, and that change is measured as a representation of the concentration of the substance of interest as a portion of the radiation was previously absorbed by the substance to be analyzed.

The German Pat. No. 730,478 discloses such an analyzer in which, moreover, two beams are provided, and the second one traverses a reference cell before reaching a (second) receiving cell. Further, both beams are modulated by a chopper, and the output is generated by comprising electrically, e.g., the pressures in the two receiver cells.

This particular type of analyzer has been practiced with advantage, but its application is somewhat limited. The limitation arises from the requirement that the gas component to be detected should not have a common absorbtion band with the host gas (host gas plus component gas constitute the measuring gas). If there are overlapping bands, errors arise. One has attempted in many ways to eliminate this phenomenon, also termed cross sensitivity.

German printed patent application No. 25 52 165, page 6, mentions the use of interference filters which eliminates those portions in and from the radiation spectrum in the test beams which fall into that overlapping range or ranges. Unfortunately, the loss in useful radiation is a considerable one. Moreover, it is very difficult in many cases to make such a filter which is really effective in the elimination of the overlapping band portions.

U.S. Pat. No. 2,761,067 suggests to eliminate the cross sensitivity by means of using measuring and reference beams of different wavelength and differently long chambers for the sample gas in both beam paths. This approach was found impractical as the reference beam in this case is not really a reference beam, and poses other problems.

DESCRIPTION OF THE INVENTION

It is an object of the present invention to provide a new and improved nondispersive infrared gas analyzer, the improvement being related towards the suppression of cross sensitivity as defined.

It is a specific object of the present invention to improve the selectivity and sensitivity of nondispersive infrared gas analyzer, using two modulated beams and receiver cells for the beams, and means for being responsive to differences in the beam absorbtion by the two cells; for example, a pressure differential chamber and a capacitive pickup, responding to such pressure difference.

In accordance with the preferred embodiment of the present invention, it is suggested to provide a measuring and reference system in and for a gas analyzer, as per the specific object, by using two significantly differently long cells for the measuring gas in the two beam paths and by including at least one interference filter in the path with the longer cell which filter eliminates to a substantial degree radiation in the overlapping portion of the absorbtion bands of the gas to be detected and of the host gas, or of one or more components thereof. The filter does not have to eliminate completely that overlapping portion, a more or less significant attenuation suffices. The inclusion of a small, but still noticeable portion of the measuring gas in the second beam obviates the need for complete suppression of radiation of the overlapping band portion in the beam path containing the longer measuring cell. It was found empirical for several instances that the cross sensitivity can be eliminated or at least reduced in order to be no longer noticeable.

Moreover, a portion of the particular beam may be permitted to pass completely unattenuated, to increase the overall gain.

DESCRIPTION OF THE DRAWINGS

FIG. 1 is a schematic view of an infrared gas analyzer constructed in accordance with the preferred embodiment; and FIG. 2 is a similar view, but showing a modification found to be suitable for specific applications.

Proceeding now to the detailed description of the drawings, FIG. 1 illustrates a source 1 of infrared radiation from which the radiation is guided into two different paths by means of a guiding and beam divider equipment 2, having two separate exit windows 2a and 2b for defining and establishing two infrared beams, respectively, along paths -a and -b. The path -a may serve as measuring beam path and -b can be termed the reference beam path.

A chopper wheel 3, having spokes and openings and being driven by a constant speed motor, rotates in front of these two windows 2a and 2b to alternately interrupt the two beams. The beams are, therefore, modulated. The gas to be analyzed (host plus component to be detected) flows into and through a small cell 5 in path -b and from there into and through a comparatively long cell 4 in path -a. It was found that the lengths of these two cells may have a ratio in the range of from 1:5 to 1:1000.

Another cell 6 is disposed in reference path -b and is filled with a gas which does not absorb infrared radiation, at least not in the band ranges of interest. This cell is provided merely to establish symmetry in the two paths as far as cell length is concerned. The several cells have appropriate entrance and exit windows. Conceivably, the window thickness may be chosen so that the sums' total in the two paths are equal.

The beams, after having traversed, respectively, cells 4, 5, and 6, reach detector cells 7 and 8, being of similar size and dimensions and being filled with gas of the kind to be detected. The two cells connect to a differential pressure chamber 9 which is divided by a membrane or diaphragm 10 pertaining to a capacitor. The capacitance of this membrane capacitor varies upon deflection of the membrane, the deflection being the result of a difference in pressure in the partitioned chamber 9.

Reference numeral 11 refers to an interference filter which is disposed between cells 4 and 7 and, thus, modifies the measuring beam. The filter can be shifted transversely to the propagation path of the beam, and it can also be tilted; both, freedom of movement and freedom of adjustability are identified by arrows. It is an important feature of the invention that the interference filter 11 does not have to intercept the entire radiation of path -a. Only a more or less significant portion needs to be intercepted, a still significant portion may be permitted to pass unaffected so that the total intensity of the beam is not excessively filtered out.

The band width of interference filter 11 is chosen so that an absorbtion edge is situated in the range of overlapping absorbtion bands of the component of interest and of the host gas, or of one or more components thereof. The filter passes freely the nonoverlapping portions of either band. Tilting shifts the absorption versus transmission ranges and, thus, permits tuning of the filter to the overlapping band. It should be noted, however, that complete elimination of radiation, having frequency in the overlapping band portions, is not necessary so that the entire interferometric attenuation is not very critical.

The reference path -b includes a diaphragm 12, also being adjustable, to trim the intensity level of the reference beam so that a particular zero reading for a measuring gas is obtained if and when the particular component to be detected is not present. Basically, the diaphragm or partial shutter 12 balances the overall beam intensities in the two paths and offsets the effect of the interference filter in path -a as to such overall intensity.

This arrangement does already provide for significant suppression of cross sensitivity. The suppression can be rendered more effective by appropriate selection of the length of short cell 5. Essential here is that this path experiences also absorption by the measuring gas, but to a lesser extent. This absorption, including absorption in the overlapping band range, in combination with the adjusted disposition of filter 11 for permitting some radiation to remain unaffected by the filter, produces the desired suppression of cross sensitivity.

The following is an example in which the invention was practiced with advantage. The task was to measure the hexane content in the exhaust gas of an automobile engine. The measuring range is from zero to 300 ppm. Cell 4 was chosen to be 190 mm long for a ratio of 950:1. Host gas in this instance is a mixture of various gases, including air, and also present is $CO_2$, which has an overlapping absorption band with hexane. Nevertheless, it was found that a 15% $CO_2$ content falsified the reading only by 1 ppm hexane near the upper range, which means, a detection error will be below 1%. 10% CO and a steam (water vapor) content corresponding to saturation at 20° C. did not have any significant influence at all.

The analyzer depicted in FIG. 2 has all of the components 1 through 11, as shown in FIG. 1, except that the balancing cell 6 of FIG. 1 is replaced by one (6') that is shorter but fulfills the same function. Moreover, there are the following additional differences between the two devices. A cell 13, filled with the component to be detected, is placed in front of receiving cell 8. In addition, another tiltable and shiftable interference filter 14 is placed in reference path -b, between cells 6' and 13. The filter is of the same type as filter 11.

This particular example of the preferred embodiment of the invention will be used with advantage if the host gas for the component of interest actually includes components having absorption bands which completely overlap one or more absorption bands of the component of interest. Proper adjustment of both filters permits even for such a severe case that the cross sensitivity be suppressed.

This particular example was practiced for detecting NO in the exhaust fumes of an automobile. These fumes (host) may also contain 10% CO and 16% $CO_2$ as well as saturated steam for for 24° C. The NO absorption bands completely overlap the absorption bands of water. Still, the measuring error could be reduced to below 1% for a 500 ppm NO content as compared to the measured NO content. Contrary thereto, an unmodified arrangement without the error compensation device would produce an error of up to 20% for a 500 ppm No content.

The invention is not limited to the embodiments described above, but all changes and modifications thereof not constituting departures from the spirit and scope of the invention are intended to be included.

We claim:

1. Nondispersive infrared gas analyzer which includes a particular component in a host gas, the host gas including at least one component having one or more infrared absorption bands which overlap an infrared absorption band of the particular component, the analyzer including a measuring beam path and a reference beam path and some means for providing infrared radiation beams of the same frequency band to the two paths, further including modulating means for the beams, the improvement comprising in combination:

a first, relatively short cell, being passed through by the gas to be analyzed and being disposed in one of said paths;

a second, relatively long cell, being also passed through by the gas to be analyzed and being disposed in another one of said paths;

a pair of receiver cells disposed respectively in said paths and being filled with the gas of said particular component;

differential pressure-sensing means coupled to the receiver cells and producing a signal representative of the concentration of the particular component in the host gas; and an interference filter in the beam path which includes the second, long cell, the filter having an absorption characteristic for a range of said overlapping absorption bands, but passing nonoverlapping portions of the absorption bands of the particular component, the filter having a disposition to permit a portion of the respective beam to pass without filtering.

2. Analyzer as in claim 1, said filter being disposed for tilting to assume an oblique position to the beam traversing the filter.

3. Nondispersive infrared gas analyzer which includes a particular component in a host gas, the host gas including at least one component having one or more infrared absorption bands which overlap an infrared absorption band of the particular component, the analyzer including a measuring beam path and a reference beam path and some means for providing infrared radiation beams of the same frequency band to the two paths, further including modulating means for the beams, the improvement comprising in combination:

a first, relatively short cell, being passed through by the gas to be analyzed and being disposed in one of said paths;

an interference filter having an absorption edge in a range of said overlapping bands, and being disposed in the beam path which includes the first cell;

an additional cell, also disposed in latter said beam path and being filled with the particular component gas;

a second, relatively long cell being also passed through the gas to be analyzed and being disposed in another one of said paths;

a second interference filter in the beam path which includes the second, long cell, the second filter also having an absorption characteristic for said range of said overlapping absorption bands, but passing nonoverlapping portions of the absorption bands of the particular component;

a pair of receiver cells disposed respectively in said paths and being filled with the gas of said particular component;

differential pressure-sensing means coupled to the receiver cells and producing a signal representative of the concentration of the particular component in the host gas.

4. Analyzer as in claim 1, or 3 wherein the first and second cells have a length ratio of from 1:5 to 1:1000.

5. Analyzer as in claim 3, at least one of the filters being disposed to permit a portion of the respective beam to pass without filtering.

6. Analyzer as in claim 5, at least one of the filters being also tiltable.

* * * * *